United States Patent
Huang et al.

(10) Patent No.: US 7,405,067 B2
(45) Date of Patent: Jul. 29, 2008

(54) BACTERIAL STRAIN FOR DEGRADATION OF ORGANIC POLYMERS AND ENVIRONMENTAL HORMONES

(75) Inventors: Shir-Ly Huang, Jungli (TW); Hsiao-Cheng Hsieh, Jungli (TW)

(73) Assignee: National Central University, Taoyuan (TW)

( * ) Notice: Subject to any disclaimer, the term of this patent is extended or adjusted under 35 U.S.C. 154(b) by 392 days.

(21) Appl. No.: 10/984,534

(22) Filed: Nov. 8, 2004

(65) Prior Publication Data
US 2005/0215619 A1   Sep. 29, 2005

(30) Foreign Application Priority Data
Nov. 6, 2003   (TW)   ............... 92131039 A

(51) Int. Cl.
*C12N 1/20* (2006.01)
*A01N 63/00* (2006.01)

(52) U.S. Cl. ................. 435/253.3; 424/93.47

(58) Field of Classification Search ............... None
See application file for complete search history.

(56) References Cited

OTHER PUBLICATIONS

John et al., J. of Bacteriology, 1998, vol. 180, pp. 4332-4338.*
Sato et al., Polymer degradation and stability 2001, vol. 74, No. 1, pp. 69-75.*
Maki et al. (1994) Degradation of alkylphenol ethoxylates by *Pseudomonas* sp. strain TR01. Appl. Environ. Microbiol. 60, 2265-2271.*
Tidswell et al., Microbiology, vol. 142, 1123-1131, 1996.*

* cited by examiner

*Primary Examiner*—Irene Marx
(74) *Attorney, Agent, or Firm*—J.C. Patents

(57) ABSTRACT

A Gram-negative bacterial strain, *Pseudomonas putida* TX2 (PTA-6169 and BCRC 910232), was isolated from farmland, which had received frequent applications of a various pesticides and surfactants. This strain was demonstrated to have the capacity to grow on alkylphenol polyethoxylates (0.05% to 20%) or alkylphenol (0.001% to 0.01%) as sole source of carbon and energy. The metabolic activity of this strain can be applied in the degradation of organic polymers containing ethoxylate units, alkylphenol and alkylphenol derivatives.

8 Claims, 4 Drawing Sheets

```
         10         20         30         40         50         60
TGCAAGTCGA GCGGATGACG GGAGCTTGCT CCTTGATTCA GCGGCGGACG GGTGAGTAAT
         70         80         90        100        110        120
GCCTAGGAAT CTGCCTGGTA GTGGGGGACA ACGTTTCGAA AGGAACGCTA ATACCGCATA
        130        140        150        160        170        180
CGTCCTACGG GAGAAAGCAG GGGACCTTCG GGCCTTGCGC TATCAGATGA GCCTAGGTCG
        190        200        210        220        230        240
GATTAGCTAG TTGGTGAGGT AATGGCTCAC CAAGGCGACG ATCCGTAACT GGTCTGAGAG
        250        260        270        280        290        300
GATGATCAGT CACACTGGAA CTGAGACACG GTCCAGACTC CTACGGGAGG CAGCAGTGGG
        310        320        330        340        350        360
GAATATTGGA CAATGGGCGA AAGCCTGATC CAGCCATGCC GCGTGTGTGA AGAAGGTCTT
        370        380        390        400        410        420
CGGATTGTAA AGCACTTTAA GTTGGGAGGA AGGGCAGTAA GTTAATACCT TGCTGTTTTG
        430        440        450        460        470        480
ACGTTACCGA CAGAATAAGC ACCGGCTAAC TCTGTGCCAG CAGCCGCGGT AATACAGAGG
        490        500        510        520        530        540
GTGCAAGCGT TAATCGGAAT TACTGGGCGT AAAGCGCGCG TAGGTGGTTC GTTAAGTTGG
        550        560        570        580        590        600
ATGTGAAAGC CCCGGGCTCA ACCTGGGAAC TGCATCCAAA ACTGGCGAGC TAGAGTACGG
        610        620        630        640        650        660
TAGAGGGTGG TGGAATTTCC TGTGTAGCGG TGAAATGCGT AGATATAGGA AGGAACACCA
        670        680        690        700        710        720
GTGGCGAAGG CGACCACCTG GACTGATACT GACACTGAGG TGCGAAAGCG TGGGGAGCAA
        730        740        750        760        770        780
ACAGGATTAG ATACCCTGGT AGTCCACGCC GTAAACGATG TCAACTAGCC GTTGGAATCC
        790        800        810        820        830        840
TTGAGATTTT AGTGGCGCAG CTAACGCATT AAGTTGACCG CCTGGGGAGT ACGGCCGCAA
        850        860        870        880        890        900
GGTTAAAACT CAAATGAATT GACGGGGGCC CGCACAAGCG GTGGAGCATG TGGTTTAATT
        910        920        930        940        950        960
CGAAGCAACG CGAAGAACCT TACCAGGCCT TGACATGCAG AGAACTTTCC AGAGATGGAT
        970        980        990       1000       1010       1020
TGGTGCCTTC GGGAACTCTG ACACAGGTGC TGCATGGCTG TCGTCAGCTC GTGTCGTGAG
       1030       1040       1050       1060       1070       1080
ATGTTGGGTT AAGTCCCGTA ACGAGCGCAA CCCTTGTCCT TAGTTACCAG CACGTTATGG
       1090       1100       1110       1120       1130       1140
TGGGCACTCT AAGGAGACTG CCGGTGACAA ACCGGAGGAA GGTGGGGATG ACGTCAAGTC
       1150       1160       1170       1180       1190       1200
ATCATGGCCC TTACGGCCTG GGCTACACAC GTGCTACAAT GGTCGGTACA GAGGGTTGCC
       1210       1220       1230       1240       1250       1260
AAGCCGCGAG GTGGAGCTAA TCTCACAAAA CCGATCGTAG TCCGGATCGC AGTCTGCAAC
       1270       1280       1290       1300       1310       1320
TCGACTGCGT GAAGTCGGAA TCGCTAGTAA TCGCGAATCA GAATGTCGCG GTGAATACGT
       1330       1340       1350       1360       1370       1380
TCCCGGGCCT TGTACACACC GCCCGTCACA CCATGGGAGT GGGTTGCACC AGAAGTAGCT
       1390       1400
AGTCTAACCT TCGGGAGGAC GGTACCAC
```

FIG. 1

SEQUENCE LISTING

<160> NUMBER OF SEQ ID NOS: 1

<210> SEQ ID NO 1
<211> LENGTH: 1408
<212> TYPE: DNA
<213> ORGANISM: Pseudomonas putida

<400> SEQUENCE: 1

-continued

```
tgcaagtcga gcggatgacg ggagcttgct ccttgattca gcggcggacg ggtgagtaat      60
gcctaggaat ctgcctggta gtgggggaca acgtttcgaa aggaacgcta ataccgcata     120
cgtcctacgg gagaaagcag gggaccttcg ggccttgcgc tatcagatga gcctaggtcg     180
gattagctag ttggtgaggt aatggctcac caaggcgacg atccgtaact ggtctgagag     240
gatgatcagt cacactggaa ctgagacacg gtccagactc ctacgggagg cagcagtggg     300
gaatattgga caatgggcga aagcctgatc cagccatgcc gcgtgtgtga agaaggtctt     360
cggattgtaa agcactttaa gttgggagga agggcagtaa gttaatacct tgctgttttg     420
acgttaccga cagaataagc accggctaac tctgtgccag cagccgcggt aatacagagg     480
gtgcaagcgt taatcggaat tactgggcgt aaagcgcgcg taggtggttc gttaagttgg     540
atgtgaaagc cccgggctca acctgggaac tgcatccaaa actggcgagc tagagtacgg     600
tagagggtgg tggaatttcc tgtgtagcgg tgaaatgcgt agatatagga aggaacacca     660
gtggcgaagg cgaccacctg gactgatact gacactgagg tgcgaaagcg tggggagcaa     720
acaggattag ataccctggt agtccacgcc gtaaacgatg tcaactagcc gttggaatcc     780
ttgagatttt agtggcgcag ctaacgcatt aagttgaccg cctggggagt acggccgcaa     840
ggttaaaact caaatgaatt gacggggccc cgcacaagcg gtggagcatg tggtttaatt     900
cgaagcaacg cgaagaacct taccaggcct tgacatgcag agaactttcc agagatggat     960
tggtgccttc gggaactctg acacaggtgc tgcatggctg tcgtcagctc gtgtcgtgag    1020
atgttgggtt aagtcccgta acgagcgcaa cccttgtcct tagttaccag cacgttatgg    1080
tgggcactct aaggagactg ccggtgacaa accggaggaa ggtggggatg acgtcaagtc    1140
atcatggccc ttacggcctg ggctacacac gtgctacaat ggtcggtaca gagggttgcc    1200
aagccgcgag gtggagctaa tctcacaaaa ccgatcgtag tccggatcgc agtctgcaac    1260
tcgactgcgt gaagtcggaa tcgctagtaa tcgcgaatca gaatgtcgcg gtgaatacgt    1320
tcccgggcct tgtacacacc gcccgtcaca ccatgggagt gggttgcacc agaagtagct    1380
agtctaacct tcgggaggac ggtaccac                                       1408
```

BACTERIAL STRAIN FOR DEGRADATION OF ORGANIC POLYMERS AND ENVIRONMENTAL HORMONES

CROSS-REFERENCE TO RELATED APPLICATION

This application claims the priority benefit of Taiwan application Ser. No. 92131039, filed on Nov. 6, 2003.

BACKGROUND OF THE INVENTION

1. Field of the Invention

The present invention relates to a bacterial strain. More particularly, the present invention relates to a bacterial strain for degrading organic polymer compounds and environmental hormone compounds.

2. Description of Related Art

Currently, organic polymers are extensively used in the agricultural, the manufacturing, the cosmetic and the medical industries. Nonionic surfactant is a typical type of organic polymers. About 25% of the nonionic surfactants are alkylphenol polyethoxylates ($APEO_n$) including nonylphenol polyethoxylates ($NPEO_n$) and octylphenol polyethoxylates ($OPEO_n$). It is important to note that, certain short chain alkylphenol polyethoxylates (for example: alkylphenol monoethoxylate and alkylphenol diethoxylates) and some alkylphenol polyethoxylates derivatives (for example: nonylphenol and octylphenol) are considered to be compounds that show the activity of an environmental hormone. Certain environmental analysis data has also indicated that these types of metabolites are not readily degradable and easily accumulate in the environment, adversely affecting human health and ecological systems. For example, recent research reports have indicated that decreasing human sperm counts may be related to the activity of environmental hormones. Therefore, problems in ecology and human health caused by surfactants and their derivatives have gained a great deal of attention in recent years.

Due to the absence of legal regulation, organic polymers, for example surfactants, are used in many industries and are often directly discharged into the natural environment along with wastewater. Furthermore, many farmlands are frequently sprayed with the pesticides and herbicides that contain a large amount of organic polymers, directly contaminating soils and fresh water.

Since the contamination of fresh water and soils by nonionic surfactant has become a serious problem in many countries, treatment methods for water and soils contaminated by nonionic surfactant are urgently required. Additionally, in the bioremediation of petroleum and petrochemical contamination, organic polymers such as surfactants are added to enhance the biodegradability of petrochemical contaminants. To prevent further contamination during the bioremediation process, the removal of the surfactants is crucial.

SUMMARY OF THE INVENTION

Accordingly, the present invention provides a bacterial strain that is able to degrade organic polymer compounds and environmental hormone compounds. The bacterial strain of the present invention is capable of degrading alkylphenol polyethoxylate type nonionic surfactants and their metabolites that have activity as an environmental hormone in order to resolve the problems of environmental pollution.

The present invention provides a bacterial strain useful in degrading organic polymer compounds and environmental hormone compounds. The bacterial strain of the invention has been deposited at Bioresources Collection and Research Center, Food Industry Research and Development Institute of Republic of China (Taiwan) on Oct. 7, 2003, with the depository number is BCRC910228. The bacterial strain of this invention has also been deposited at the American Type Culture Collection (ATCC) in the United States of America on Aug. 26, 2004 with the depository number PTA-6169. The bacterial strain is a Gram-negative rod-shaped bacterium and was isolated from farmlands that had frequent applications of a variety of surfactants and pesticides. This bacterial strain, under the appropriate cultivation conditions, can degrade both alkylphenol polyethoxylate compounds and alkylphenol compounds. The range over which degradation of the compounds occurs is 0.05% to 20% for alkylphenol polyethoxylate compounds and 0.001% to 0.01% for the alkylphenol compounds when they are sole carbon source and energy source.

This bacterial strain can effectively degrade alkylphenol polyethoxylate compounds and alkylphenol compounds, and therefore can be used to remove contamination by nonionic surfactants. Thus, it can be applied to the bioremediation of water and soil. Further, it has great potential for degrading other organic polymers and environmental hormone compounds.

The above is a brief description of some deficiencies in the prior art and advantages of the present invention. Other features, advantages and embodiments of the invention will be apparent to those skilled in the art from the following description, accompanying drawings and appended claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1 is the 16S rDNA sequence of the bacterium of the present invention according to one embodiment of the invention.

DESCRIPTION OF THE PREFERRED EMBODIMENTS

Figure 2:
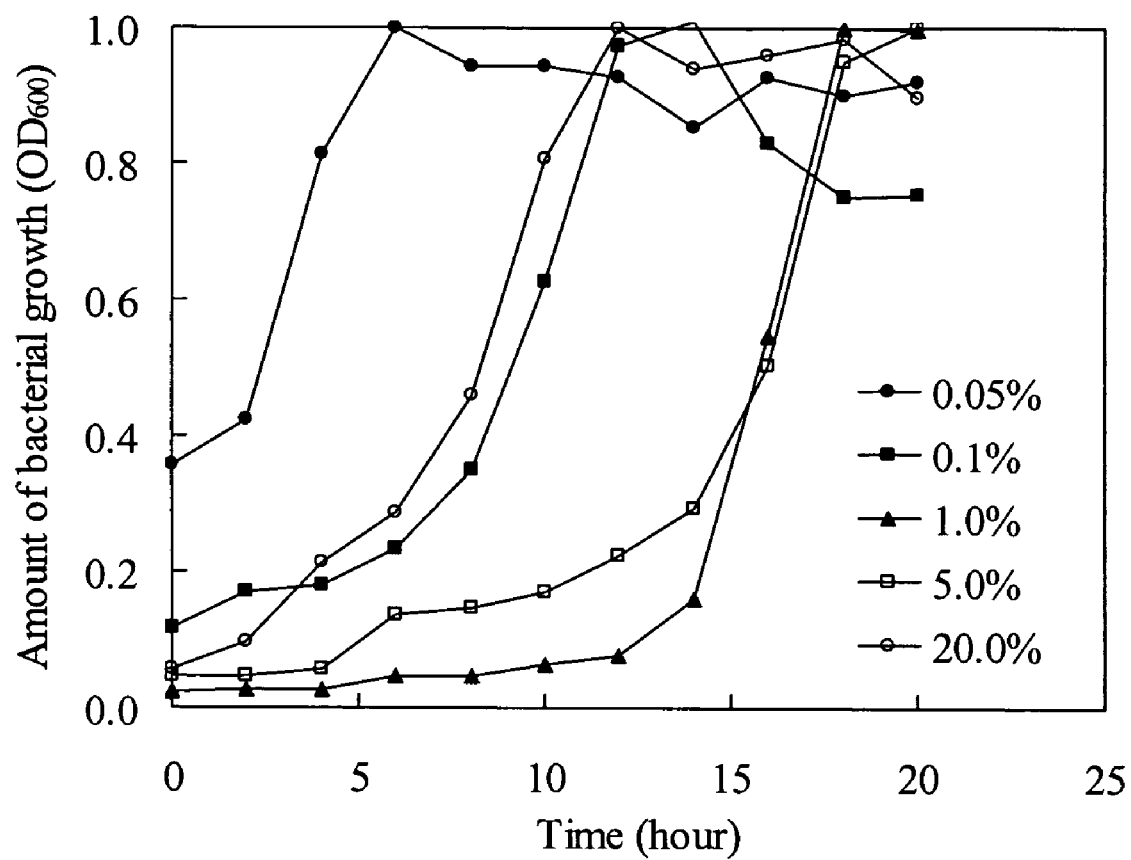
FIG. 2 is a diagram illustrating the relationship between the amounts of bacteria growth and cultivation time in an environment having various concentrations of the alkylphenol polyethoxylate compound as sole carbon source according to one embodiment of the invention.

The present invention provides a bacterial strain that can effectively degrade organic polymer compounds and their metabolites that have activity as an environmental hormone. These compounds are often used in general manufacture industries and agricultural activities. The bacterial strain of the invention is capable of degrading organic polymer compounds including but not limited to, for example, the alkylphenol polyethoxylate type of nonionic surfactants and derivatives containing alkylphenol units. Accordingly, the contamination problems of soil and fresh water due to organic polymer compounds and environmental hormone compounds can thus be resolved.

The bacterial strain of the invention was deposited at Bioresources Collection and Research Center, Food Industry Research and Development Institute of Republic of China (Taiwan) on Oct. 7, 2003, with the depository number is BCRC910228. The bacterial strain of this invention was also deposited to the American Type Culture Collection (ATCC) in the United States of America on Aug. 26, 2004, and the depository number is PTA-6169. The bacterial strain is a Gram-negative rod-shaped bacterium.

This bacterial strain was isolated and screened from farmlands that had been sprayed with pesticides on a long-term basis. The screening method used involved using enrichment culture technology. The bacterial strain of the present invention has a variety of biochemical characteristics and these are detailed in the following paragraphs.

The bacterial strain of the present invention has been verified to be the species *Pseudomonas putida* by the Biolog method and the fatty acid fingerprinting method. FIG. 1 is the 16S rDNA sequence of the bacterium of the present invention. The analysis result from the 16S rDNA sequencing method also suggests the bacterial strain of the invention is the most similar to *Pseudomonas putida* (AY686638). However, the bacterial strain of the present invention is different from the type strain of *Pseudomonas putida*. The bacterium of the present invention is confirmed to have the capability to degrade alkylphenol polyethoxylate compounds and alkylphenol compounds. Furthermore, this bacterial strain can use octylphenol polyethoxylates (Triton X-100, where average number of ethoxylate unit is 9.5) as sole carbon source. Therefore, this particular strain is designated *P. putida* TX2.

The bacterial strain of this invention (*Pseudomonas putida* TX2) can degrade organic polymers and environmental hormone compounds. The organic polymers that can be degraded by the bacterial strain of this invention include, but are not limited to alkylphenol polyethoxylates, dodecyl octaethoxylate, polyethylene glycol, 1,4-dioxane, trioxane and cyclic ethers. The environmental hormone compounds degradable by the bacterial strain of this invention include, alkylphenols or derivatives of alkylphenol polyethoxylates. Furthermore, the bacterial strain of the present invention can grow in a culture medium that contains alkylphenol polyethoxylate compounds or alkylphenol compounds and can use alkylphenol polyethoxylate or alkylphenol as sole carbon source. To explain this in greater details, the bacterial strain of this invention can degrade alkylphenol polyethoxylate compounds or alkylphenol compounds and grow using these organic compounds or environmental hormones as sole carbon source at temperatures ranging from about 15 degrees Celsius to about 40 degrees Celsius under aerobic conditions. The chemical structure of an alkylphenol polyethoxylate is shown in expression (1)

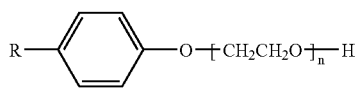

(1)

wherein when n is 1, the alkylphenol polyethoxylate is alkyphenol monoethoxylate with a chemical structure as shown below:

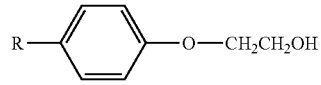

Further, if n is 2, the alkylphenol polyethoxylate is alkylphenol diethoxylate with a chemical structure as shown below:

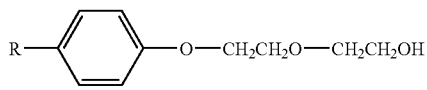

In addition, when R is an octyl group, the alkylphenol polyethoxylate is an octylphenol polyethoxylate, OPEOn).

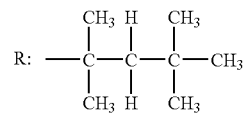

Further, if R is a nonyl group (as shown below in either a branch type or a straight chain type), the alkylphenol polyethoxylate is a nonylphenol polyethoxylate, NPEOn).

(Branch type)

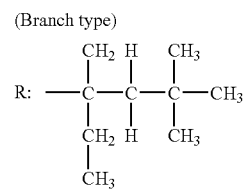

(Straight chain type)

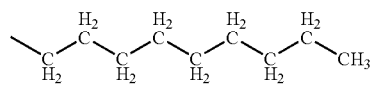

On the other hand, the chemical structure of an alkylphenol compound is shown as expression (2):

(2)

Similarly, when R is an octyl group, the alkylphenol is octylphenol. When R is a nonyl group (including branch or straight type), the alkylphenol compound is a nonylphenol compound. Further, the alkylphenol compounds include the derivatives of alkylphenol, for example, alkylcatechol with a chemical structure shown as expression (3) below:

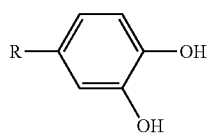

(3)

Particularly, the bacterial strain of this invention can grow in an environment that contains a wide concentration range of alkylphenol polyethoxylate compound (for example, 0.05% to 20%) or of the alkylphenol compound (for example, 0.001% to 0.01%). It is important to note that the survivability and the tolerance of this bacterial strain remain excellent even in an environment having a high alkylphenol polyethoxylate concentration (for example, 20%).

Furthermore, the growth curve of the bacterial strain of the invention using various concentrations of the alkylphenol polyethoxylate compound as sole carbon source is illustrated in FIG. 2. In FIG. 2, the x-axis is the culturing time in hours, while the y-axis is the amount of bacteria growth in the presence of various concentrations of alkylphenol polyethoxylate compound. The range of concentrations of the alkylphenol polyethoxylate compound include 0.05% (●)·0.1% (■)·1.0% (▲)·5.0% (□) 20.0% (○). Further, the amount of bacteria growth is based on the absorbance at a wavelength of 600 nm measured by a spectrophotometer, and is standardized by the maximum amount of bacteria growth. As clearly illustrated in FIG. 1, the bacterial strain of this invention is able to grow in an environment that contains a very wide concentration range of alkylphenol polyethoxylates (0.05% to 20.0%) as sole carbon source.

Figure 3:
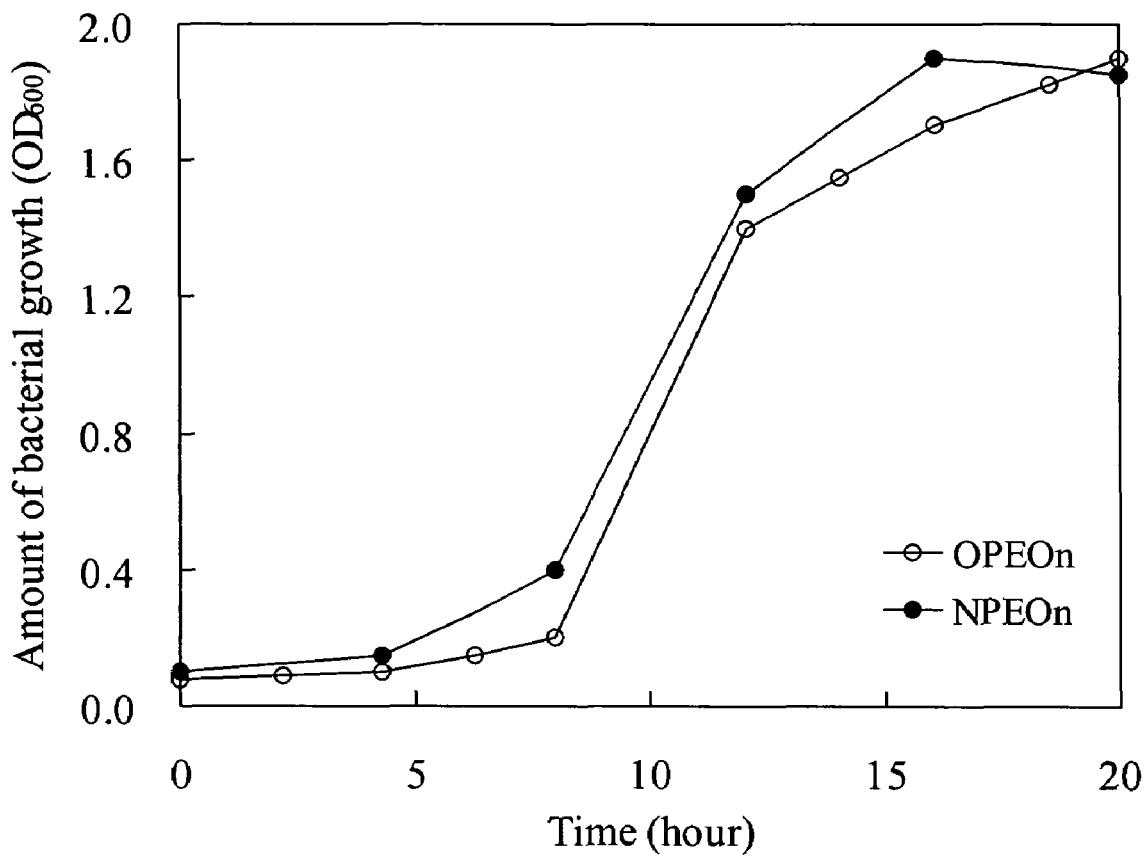
FIG. 3 is a diagram illustrating the relationship between the amounts of bacteria growth and cultivation time in an environment having a 0.5% of nonylphenol polyethoxylates (NPEOn) compound and 0.5% of octylphenol polyethoxylates (OPEOn) compound as sole carbon source according to one embodiment of the invention.
Figure 4:
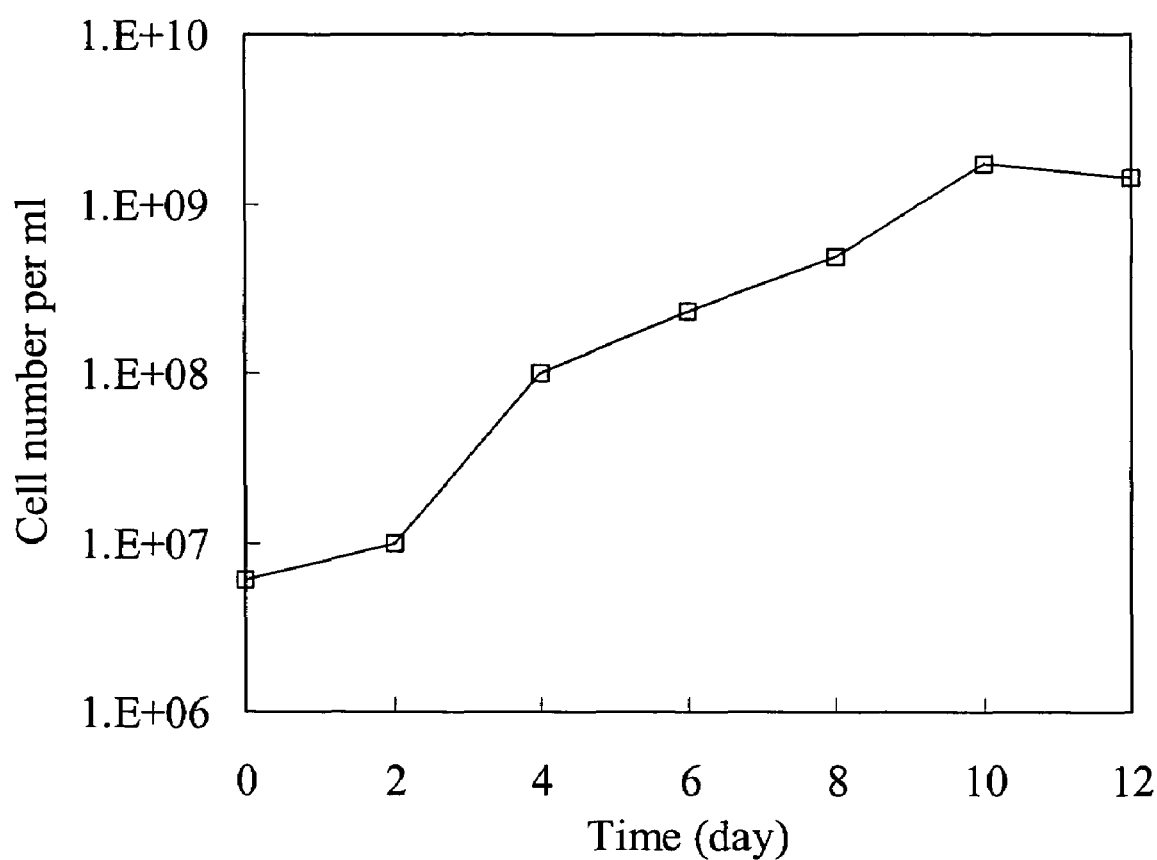
FIG. 4 is a diagram illustrating the relationship between the amounts of bacteria growth and cultivation time in an environment having a 0.005% of the octylphenol (OP) compound as sole carbon source according to one embodiment of the invention.

The growth curves of the bacterial strain of this invention cultured in the presence of 0.5% of the nonylphenol polyethoxylate (NPEOn) compound (●), 0.5% of the octylphenol polyethoxylate (OPEOn) compound (○) and 0.005% of the octylphenol (OP) compound (□) as sole carbon source are illustrated in FIG. 3 and FIG. 4, respectively. As shown in FIG. 3 and FIG. 4, the x-axis represents time in hour, while the y-axis represents the corresponding bacteria growth under a culturing environment with 0.5% of the nonylphenol polyethoxylate compound and 0.5% of the octylphenol polyethoxylate compound in FIG. 3, and 0.005% of an octylphenol compound in FIG. 4, respectively. The amount of bacteria growth is based on the absorbance readings at a wavelength of 600 nm using a spectrophotometer or cell numbers per ml. As clearly illustrated in FIG. 3 and FIG. 4, the bacterial strain of this invention can grow in a culturing environment using an alkylphenol polyethoxylate compound or an alkylphenol compound as sole carbon source. Moreover, alkylphenol, a metabolite of alkylphenol polyethoxylate with activity as an environmental hormone, is often accumulated in the environment. When the bacterial strain of this invention is used to degrade alkylphenol polyethoxylate, the metabolite generated, alkylphenol, can further be degraded by the bacterial strain. The bacterial strain continues to survive using alkylphenol as the sole carbon source.

Based on the oxygen consumption activity analysis, the bacterial strain of this invention showed high oxygen consumption activity when degrading alkylphenol polyethoxylate or alkylphenol compounds. Based on this analysis, it was shown that bacteria with growth turbidity in the range of 0.3 to 0.5 (based on the absorbance measurement at 600 nm using a spectrophotometer) have an oxygen consumption activity that is between about 1 nmole/min and about 150 nmole/min.

Accordingly, the bacterial strain of the invention can degrade organic polymers (for example, nonionic surfactant) and environmental hormones (for example, the metabolites of nonionic surfactant), and can use the organic polymers and environmental hormones as sole carbon source. Therefore, this bacterial strain has potential practical applications in the treatment of environmental contamination, including but not limited to soil remediation and the treatment of contaminated water.

Moreover, the bacterial strain of the present invention, not only can degrade alkylphenol polyethoxylate type organic polymers, but it can also effectively degrade their metabolites that have activity as environmental hormones or other organic polymers or other environmental hormones that have a similar structure.

The foregoing description of the preferred embodiment of the present invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode of practical application, thereby to enable persons skilled in the art to understand the invention's various embodiments and the various modifications as are suited to the particular use or implementation contemplated. It is intended that the scope of the invention be defined by the claims appended hereto and their equivalents in which all terms are meant in their broadest reasonable sense unless otherwise indicated. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed:

1. A biologically pure culture of the bacterial strain *Pseudomonas putida* TX2 (BCRC 910232) which degrades the organic polymers alkylphenol polyethoxylates, polyethylene glycol, dodecy octaethoxylate, 1,4-dioxane, trioxane or cyclic ethers, and the environmental hormone alkylphenols, and which is capable to grow in a culture medium containing alkylphenol polyethoxylates with a concentration of about 0.05% to about 20%.

2. The bacterial strain of claim 1, wherein the bacterial strain is a Gram-negative rod-shaped bacterium.

3. The bacterial strain of claim 1, wherein the bacterial strain grows in a culturing medium using the organic polymer or the environmental hormone as a sole carbon source under an aerobic condition at a temperature of about 15 degrees Celsius to about 40 degrees Celsius.

4. The bacterial strain of claim 3, wherein the bacterial strain grows in the culturing medium that comprises 0.001% to 0.01% of the alkylphenols.

5. The bacterial strain of claim 4, wherein the bacterial strain has a generation time of about 1 to 4 hours in the culture medium that contains the alkylphenol polyethoxylates or below 40 hours in the culture medium that contains the alkylphenols.

6. The bacterial strain of claim 4, wherein an oxygen consumption activity of the bacterial strain during a transformation of the alkylphenol polyethoxylates or the alkylphenols is between about 1 nmole/min to 150 nmole/min.

7. The bacterial strain of claim 4, wherein the alkylphenol polyethoxylates are octylphenol polyethoxylates or nonylphenol polyethoxylates.

8. The bacterial strain of claim 4, wherein the alkylphenols are octylphenols, nonylphenols, butylphenols or ethylphenols.

* * * * *